United States Patent [19]

Ryugo

[11] Patent Number: Plant 6,452

[45] Date of Patent: Dec. 6, 1988

[54] PEAR TREE—'ELLIOT'

[75] Inventor: Kay Ryugo, Davis, Calif.

[73] Assignee: Regents of the University of California, Berkeley, Calif.

[21] Appl. No.: 20,911

[22] Filed: Mar. 2, 1987

[51] Int. Cl.[4] ..... A01H 5/03

[52] U.S. Cl. ..... Plt./36

[58] Field of Search ..... Plt./36

*Primary Examiner*—Robert E. Bagwill

*Attorney, Agent, or Firm*—Townsend and Townsend

[57] ABSTRACT

A new and distinct variety of pear tree primarily characterized by its tolerance to the fire-blight organism. (*Erwinia amylovora*), and further characterized by a blooming habit concurrent with 'Bartlett'; skin with firm and buttery texture, and fruit with a flavor which is excellent to good. The keeping quality of the fruit is good to excellent.

3 Drawing Sheets

This invention relates to a new variety of pear tree; (*Pyrus communis*), characterized by its tolerance to the fire-blight organism; *Erwinia amylovora.*

The new variety is a progeny of a cross between 'Elliot No. 4' (female parent) and 'Vermont Beauty' (pollen parent). 'Elliot No. 4' was discovered as a rootstock sucker on the Elliot Ranch in the Sacramento River delta by Dr. Harvey E. Thomas, Plant Pathologist at the University of California, Berkeley, Calif. In the early 1930's a grafted plant of 'Elliot No. 4' was given to Dr. Luther D. Davis, a faculty member in the Department of Pomology of the University of California.

In 1964 'Elliot No. 4' was crossed with 'Vermont Beauty'. Seeds germinated in 1965 and were grown in the University's Davis nursery. Hybrid seedlings of the cross were transplanted in 1967 at their present location in Davis, Calif. where the seedling of the variety of this invention was selected for its commercial potential.

The present variety which has been named 'Elliot' was asexually reproduced in 1982 by top-grafting on compatible pear seedlings at Davis, Calif. and, in maturity, the reproductions have proven true to the original selection in all respects.

Figure 1:
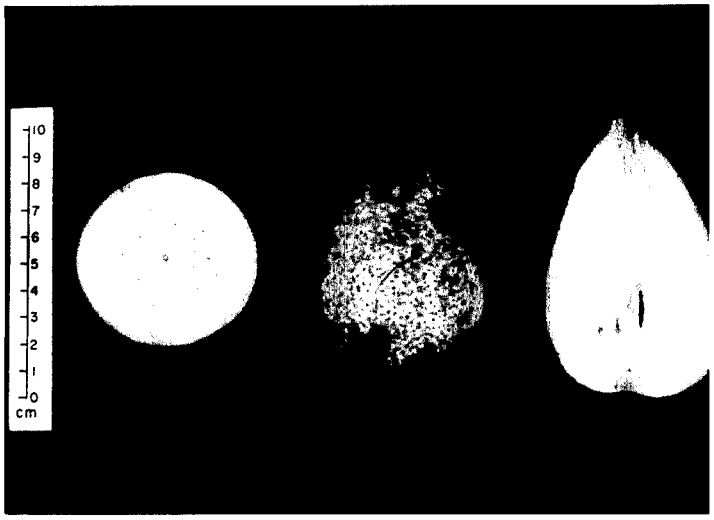
FIG. 1 shows mature fruit typical of the new variety.
Figure 2:
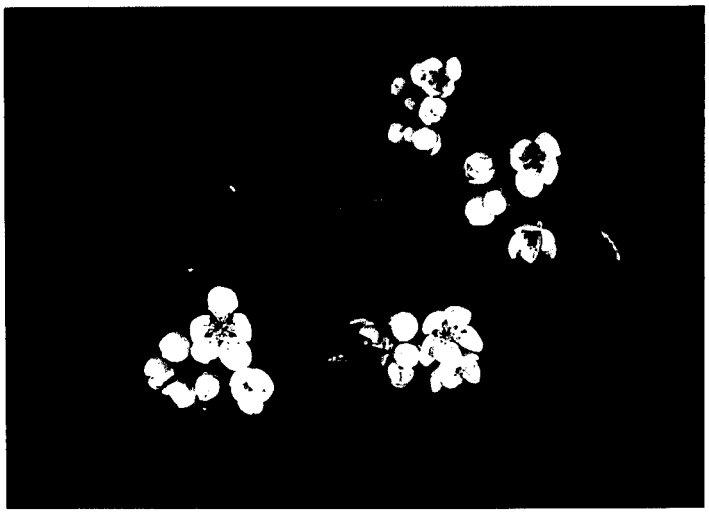
FIG. 2 shows flowering spurs of the new variety.
Figure 3:
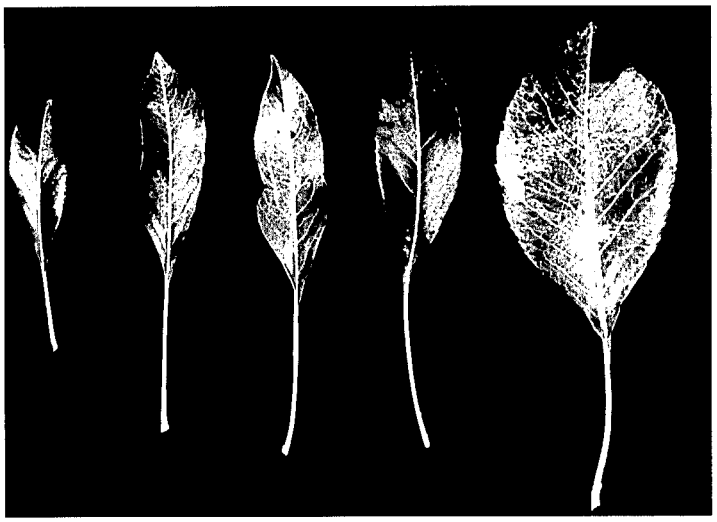
FIG. 3 shows leaves of the new variety.
Figure 4:
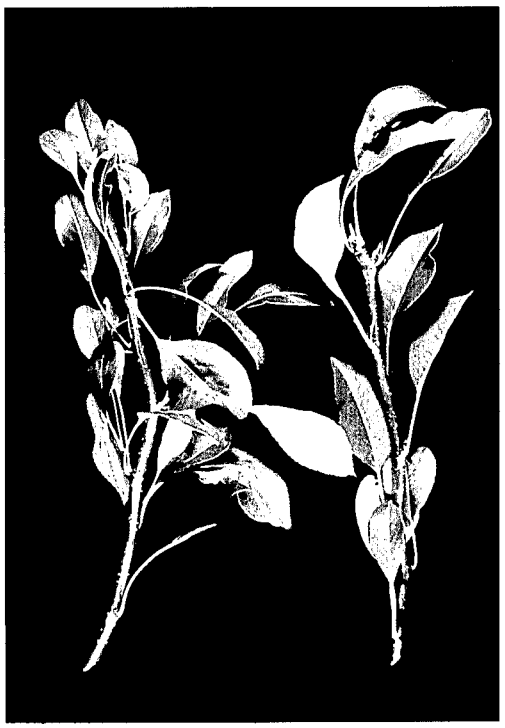
FIG. 4 illustrates growth habit.
Figure 5:
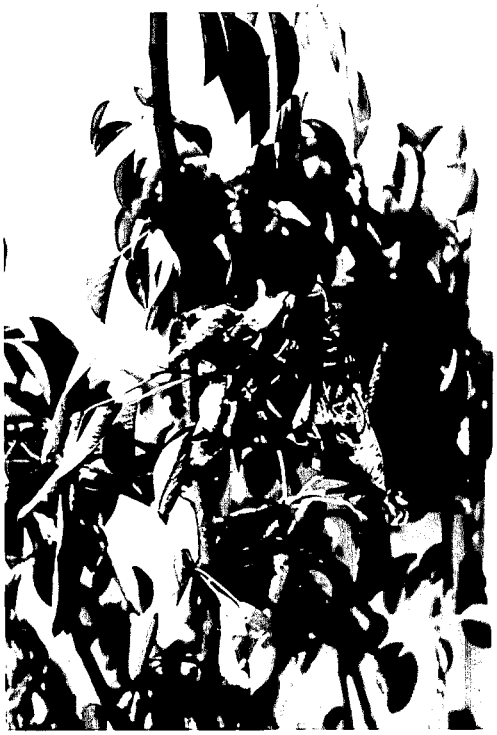
FIG. 5 shows a 'Bartlett' pear tree with fire-blight infestation.

The pear tree of the new variety blooms concurrently with 'Bartlett' and is rather vigorous. Additionally, the fruit possesses a richness of flavor and smoothness of texture superior to 'Bartlett'.

The most valuable asset of the new variety is its tolerance to the fire-blight organism, *Erwinia amylovora.* When bacterial suspension were administered to open flowers, the flowers turned black but the infection dis not invade beyond the peduncle. Under natural conditions, only two cankers have been observed since 1967. The foundation block of the variety was not sprayed with any chemical or antibiotic during the period the tree was observed.

The botanical details of the new and distinct variety of pear tree with color definitions according to Munsell Color System-Nickerson Color Fan, are as follows:

Tree: The original tree stands about 16 feet high with a trunk diameter of about 14 inches (4.9 meters tall with a diameter of 36 cm.). The trunk has a scaly bark. The growth habit is upright with narrow branching angle, typical of the European pears.

*Stem.*—Smooth epidermis, highly pigmented (2.5 R 4/10) with anthocyanin, especially on the side exposed to the sun.

*Hardiness.*—Withstands the cold of Northern California without any signs of winter injury.

*Bearing potential.*—Bears regularly; grafted trees begin to bear in the 3rd season in the orchard. Compatible with 'Winter Nelis' seedling; untested on Quince rootstocks.

Leaves:

*Size and shape.*—Elliptical, the length ranging from 5.1 to 8.9 cm and the width ranging from 1.8 to 4.7. The mean length width ratio is 1.9:1.0. Apices are acute to murconate; margins are finely serrate.

*Petiole.*—Slender, approximately equal in length to the leaf blade, and occasionally stipulate.

*Adaxial or upper side.*—Glabrous or glossy, and smooth.

*Abaxial or under side.*—Dull.

Flowers: The mixed buds contain 2 to 7 flowers.

*Bloom date.*—Depending on the cold hours, anthesis is from middle to late March, overlapping with Bartlett in most years.

*Petals.*—Average size, pinkish (10 RP 8/5) at budbreak turning white at full bloom.

*Anthers.*—Purple (2.5 P 3/8) prior to dehiscence turning black after shedding pollen. Bears fertile pollen.

Fruit:

*Size and shape.*—Pyriform and tapered slightly, lacking a distinct shoulder. Length and width range from 6–9 and 3–6 cm at maximum equatorial diameter, respectively. Pedicel is short (1 cm) and thick with a pronounced thickening at the base. Calyx lobes are mostly persistent.

*Skin color.*—Good yellow (5 Y 8/12) with slight russetting (2.5 Y 6/8 to 7/10) when ripe typical of a fall pear. Side exposed to sun tends to form reddish blush.

*Flesh color.*—White. The soluble solids content is about 18%. Core size: average to large.

*Texture.*—Buttery and tender but firm with low fiber content.

*Juice.*—Rich — not watery, not overly sweet, has body to it and a pleasant aroma.

*Flavor.*—Excellent to good. Sugar:acid ratio is well balanced; pleasant to taste.

*Keeping quality.*—Good to excellent, keeping for 3 months at 32° F. in an ambient atmosphere.

*Ripening.*—The fruit will ripen on the tree unlike many European pear cultivars.

The fruit of 'Elliott' is susceptible to attack by coddling moths but no more so than 'Bartlett' and 'Elliot' because of its tolerance to fire blight and its excellent flavor and texture should be valuable as a back yard pear tree.

I claim:

1. The new and distinct variety of pear tree herein described and illustrated and identified by the characteristics enumerated above together with the parts thereof.

* * * * *